(12) United States Patent
Lin et al.

(10) Patent No.: US 8,236,890 B2
(45) Date of Patent: Aug. 7, 2012

(54) EMULSIONS OF SILICONE ELASTOMER AND SILICONE ORGANIC ELASTOMER GELS

(75) Inventors: Shaow Burn Lin, Midland, MI (US); Jason Humphrey, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 286 days.

(21) Appl. No.: 12/680,061

(22) PCT Filed: Sep. 18, 2008

(86) PCT No.: PCT/US2008/076953
§ 371 (c)(1),
(2), (4) Date: Mar. 25, 2010

(87) PCT Pub. No.: WO2009/042509
PCT Pub. Date: Apr. 2, 2009

(65) Prior Publication Data
US 2010/0209367 A1    Aug. 19, 2010

Related U.S. Application Data

(60) Provisional application No. 60/974,873, filed on Sep. 25, 2007.

(51) Int. Cl.
*C08K 3/00* (2006.01)

(52) U.S. Cl. ........................................ 524/588; 424/401

(58) Field of Classification Search ................... 524/588; 424/401
See application file for complete search history.

(56) References Cited

U.S. PATENT DOCUMENTS

| | | | |
|---|---|---|---|
| 315,960 | A | 12/1964 | Ashby |
| 3,220,972 | A | 11/1965 | Lamoreaux |
| 3,296,291 | A | 1/1967 | Chalk et al. |
| 3,419,593 | A | 12/1968 | Willing |
| 3,516,946 | A | 6/1970 | Modic |
| 3,814,730 | A | 6/1974 | Karstedt |
| 3,928,629 | A | 12/1975 | Chandra et al. |
| 3,989,668 | A | 11/1976 | Lee et al. |
| 4,122,029 | A | 10/1978 | Gee et al. |
| 5,036,117 | A | 7/1991 | Chung et al. |
| 5,175,325 | A | 12/1992 | Brown et al. |
| 5,811,487 | A | 9/1998 | Schulz, Jr. et al. |
| 6,200,581 | B1 | 3/2001 | Lin et al. |
| 6,605,734 | B2 | 8/2003 | Roy et al. |
| 2006/0111491 | A1* | 5/2006 | Asch et al. ............ 524/261 |

FOREIGN PATENT DOCUMENTS

| WO | WO03/093349 | 11/2003 |
|---|---|---|
| WO | WO03/093369 | 11/2003 |
| WO | WO2007/109240 | 9/2007 |
| WO | WO2007/109260 | 9/2007 |
| WO | WO2007/109282 | 9/2007 |

* cited by examiner

*Primary Examiner* — Margaret Moore
(74) *Attorney, Agent, or Firm* — Alan Zombeck

(57) ABSTRACT

Aqueous emulsions are disclosed of a gel or gel paste containing a silicone elastomer from the reaction an organohydrogensiloxane having at least two SiH containing cyclosiloxane rings in its molecule and a compound having at least two aliphatic unsaturated groups in its molecule.

6 Claims, No Drawings

EMULSIONS OF SILICONE ELASTOMER AND SILICONE ORGANIC ELASTOMER GELS

CROSS REFERENCE TO RELATED APPLICATIONS

This application is a U.S. national stage filing under 35 U.S.C. §371 of PCT Application No. PCT/US08/76953 filed on Sep. 18, 2008, currently pending, which claims the benefit of U.S. Provisional Patent Application No. 60/974,873 filed Sep. 25, 2007 under 35 U.S.C. §119 (e). PCT Application No. PCT/US08/76953 and U.S. Provisional Patent Application No. 60/974,873 are hereby incorporated by reference.

TECHNICAL FIELD

This disclosure relates to aqueous emulsions of a gel or gel paste containing a silicone elastomer or a silicone organic elastomer from the reaction of an organohydrogensiloxane having at least two SiH containing cyclosiloxane rings in its molecule and a compound having at least two aliphatic unsaturated groups in its molecule.

BACKGROUND

Gels and gel pastes containing a silicone elastomer or a silicone organic elastomer have recently been described in PCT/US07/006833, PCT/US07/006894, and PCT/US07/006936; which are assigned to the same assignee of the present application. The present disclosure relates to aqueous emulsion compositions of these gels and gel pastes containing a silicone elastomer or a silicone organic elastomer.

SUMMARY

This disclosure relates to aqueous emulsions comprising:
i) a gel or gel paste containing a silicone elastomer or a silicone organic elastomer from the reaction of;
  A) an organohydrogensiloxane having at least two SiH containing cyclosiloxane rings in its molecule,
  B) a compound having at least two aliphatic unsaturated groups in its molecule, and
  C) a hydrosilylation catalyst,
  D) an optional carrier fluid, and
ii) an emulsifier.
The emulsion may further comprise E) an optional personal or healthcare active.

The present disclosure further relates to a process for preparing an aqueous emulsion comprising:
I) mixing
i) a gel or gel paste containing a silicone elastomer or a silicone organic elastomer from the reaction of;
  A) an organohydrogensiloxane having at least two SiH containing cyclosiloxane rings in its molecule,
  B) a compound having at least two aliphatic unsaturated groups in its molecule, and
  C) a hydrosilylation catalyst,
  D) an optional carrier fluid,
  E) an optional personal or healthcare active, and
ii) an emulsifier,
II) admixing incremental amounts of water to the mixture of step I to form a water continuous emulsion,
III) optionally, shear mixing the water continuous emulsion.

DETAILED DESCRIPTION

The present disclosure relates to aqueous emulsion compositions comprising; i) gel or gel paste containing a silicone elastomer or a silicone organic elastomer and ii) an emulsifier. The aqueous emulsion compositions may optionally contain E) a personal or healthcare active.

The gel or gel pastes containing a silicone elastomer or a silicone organic elastomer useful as component i) may be selected from those as described in PCT/US07/006833, PCT/US07/006894, and PCT/US07/006936, which are herein incorporated by reference for their teaching of silicone elastomer eels or gel pastes.

The gel or gel pastes useful as component contain a silicone elastomer from the reaction of;
  A) an organohydrogensiloxane having at least two SiH containing cyclosiloxane rings in its molecule,
  B) a compound having at least two aliphatic unsaturated groups in its molecule, and
  C) a hydrosilylation catalyst.
The silicone elastomer may be dispersed in;
  D) an optional carrier fluid, which when used further constitutes the eel or gel paste composition. The aqueous emulsions may optionally contain;
  E) a personal or healthcare active.

(A) The Organohydrogensiloxane Having at Least Two SiH Containing Cyclosiloxane Rings Component (A) in the present invention is an organohydrogensiloxane having at least two SiH containing cyclosiloxane rings in its molecule. Organohydrogensiloxanes suitable as component A) in the present invention are any organopolysiloxanes having in its molecule at least two cyclosiloxane rings with at least one silicon bonded hydrogen (SiH) unit on each siloxane ring. Organopolysiloxanes are well known in the art and are often designated as comprising any number of $(R_3SiO_{0.5})$, $(R_2SiO)$, $(RSiO_{1.5})$, or $(SiO_2)$ siloxy units where R is independently any organic group. When R is methyl in the siloxy unit formulas of an organopolysiloxane, the respective siloxy units are often designated as M, D, T or Q siloxy units. Cyclosiloxane rings contain at least three siloxy units (that is the minimum needed in order to form a siloxane ring), and may be any combination of $(R_3SiO_{0.5})$, $(R_2SiO)$, $(RSiO_{1.5})$, or $(SiO_2)$ siloxy units that forms a cyclic structure, providing at least one of the cyclic siloxy units on each siloxane ring contains one SiH unit, that is there is at least one $(R_2HSiO_{0.5})$, $(RHSiO)$, or a $(HSiO_{1.5})$ siloxy unit present in the ring. These siloxy units can be represented as $M^H$, $D^H$, and $T^H$ siloxy units respectively when R is methyl.

The cyclosiloxane rings of A) the organohydrogensiloxane are linked together by a divalent organic or siloxane group, or combination thereof. The divalent linking group may be designated as Y and the cyclosiloxane G. Thus, the organohydrogensiloxane of the present invention may be represented by the general formula G-[Y-G]$_a$, where G is a cyclosiloxane as described above and Y is a divalent organic, a siloxane, a polyoxyalkylene group, or combination thereof, and the subscript a is greater than zero.

When Y is a divalent organic, it may be a divalent hydrocarbon containing 1 to 30 carbons, either as aliphatic or aromatic structures, and may be branched or un-branched. Alternatively. Y can be an alkylene group containing 2 to 20 carbons, or alternatively containing 4 to 12 carbons.

When Y is a divalent organic, it may also be selected from an organic polymer, such as a polyoxyalkylene group.

When Y is a siloxane group it may be selected from any organopolysiloxane containing at least two divalent hydrocarbon groups, designated as $R^1$. Thus, the siloxane linking group can be any organopolysiloxane comprising at least two siloxane units represented by the average formula $R^1R_mSiO_{(4-m/2)}$ wherein
R is an organic group.
$R^1$ is a divalent hydrocarbon, and
m is zero to 3

The $R^1$ group may be present on any mono, di, or tri-siloxy unit in an organopolysiloxane molecule, for example; $(R^1R_2SiO_{0.5})$, $(R^1RSiO)$, or $(R^1SiO_{1.5})$, as well as in combination with other siloxy units not containing an $R^1$ substituent, such as $(R_3SiO_{0.5})$, $(R_2SiO)$, $(RSiO_{1.5})$, or $(SiO_2)$ siloxy units where R is independently any organic group providing there are at least two $R^1$ substituents in the organopolysiloxane. Representative $R^1$ groups include; ethylene, propylene, butylene, isobutylene, hexylene, and similar homologs. Alternatively, $R^1$ is ethylene.

Representative, non-limiting, examples of such siloxane based structures suitable as siloxane linking groups include;

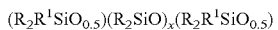

$(R_2R^1SiO_{0.5})(R_2SiO)_x(R_2R^1SiO_{0.5})$

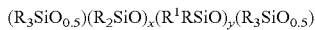

$(R_3SiO_{0.5})(R_2SiO)_x(R^1RSiO)_y(R_3SiO_{0.5})$

$(R_3SiO_{0.5})(R_2SiO)_x(R^1RSiO)_y(RSiO_{1.5})_z(R_3SiO_{0.5})$ where $x \geq 0$, $y \geq 2$, and z is $\geq 0$ Organohydrogensiloxane having at least two SiH containing cyclosiloxane rings (component A) may be prepared via a hydrosilylation reaction of a) an organohydrogencyclosiloxane having at least two SiH units on the siloxane ring and, B) a compound or mixture of compounds having at least two aliphatic unsaturated groups in its molecule, The organohydrogencyclosiloxane (a) having at least two SiH on the siloxane ring may contain any number of siloxy units as defined above) provided there are at least two SiH units on the cyclosiloxane ring. For example, the cyclic siloxane can comprise any number of M, $M^H$, D, $D^H$, or $T^H$ siloxy units. Representative, non-limiting examples of such organohydrogencyclosiloxanes useful to prepare component (A) have the average formula $D^H_a D_b$ where a is $\geq 1$ and b is $\geq 0$, and $a+b \geq 3$. Alternatively, the organohydrogencyclosiloxane may be selected from those having the formula $[(CH_3)HSiO]_g$ where g is 3-8, such as $D^H_4$, $D^H_5$, $D^H_6$, or mixtures thereof.

Suitable compounds containing at least two aliphatic unsaturated hydrocarbon groups in its molecule are described below as component B).

Hydrosilylation reactions involving organohydrogensiloxanes and unsaturated compounds are well known. Any suitable hydrosilylation catalysts know in the art may be used, or alternatively may be selected from those described below as component C). Any of the known hydrosilylation techniques and reactions may be employed to prepare component A) from i) organohydrogencyclosiloxane having at least two SiH units on the siloxane ring and, B) a compound or mixture of compounds having at least two aliphatic unsaturated groups in its molecule. However, the reaction is conducted in such a manner to provide an organohydrogensiloxane having at least two SiH containing cyclosiloxane rings in its molecule.

Thus, component A of the present invention contains at least two silicon-bonded hydrogen atom per molecule, alternatively at least 4 silicon-bonded hydrogen atoms per molecule, or alternatively at least 6 silicon-bonded hydrogen atoms per molecule. This can be accomplished by using in the hydrosilylation reaction a molar excess of the a) the organohydrogencyclosiloxane having at least two SiH units on the siloxane ring vs. the compound containing at least two aliphatic unsaturated groups in its molecule. The molar excess may be expressed as the molar ratio of SiH units to unsaturated group, such ratio may range from 2/1 to 8/1, alternatively from 2/1 to 6/1, or alternatively from 3/1 to 4/1.

Alternatively, the organohydrogensiloxane useful as component A) may be selected from any of the organohydrogensiloxanes taught in WO03/093349, which is herein incorporated by reference for its teaching of suitable organohydrogensiloxanes.

The organohydrogensiloxane useful as component A) in the present invention typically have a viscosity from 5 to 50,000 mPa·s, alternatively from 10 to 10,000 mPa·s, or alternatively from 25 to 2,000 mPa·s.

Additives known as inhibitors or stabilizers may be added to component A). Inhibitors such as those described in WO 03/093369 may be added for the purpose of stabilizing component A) during storage, or prior to the addition of component B) to prepare the silicone elastomer gel. The inhibitor may be selected from any compound known to have inhibiting effects of platinum based hydrosilylation reactions. A particularly preferred inhibitor is vitamin A palmitate, or VAP. When VAP is used, it is typically added at 0.05 to 2.0 parts per 100 parts of component A).

(B) The Compound or Mixture of Compounds Having at Least Two Aliphatic Unsaturated Hydrocarbon Groups in its Molecule Component (B) is a compound, or any mixture of compounds, containing at least two aliphatic unsaturated groups in its molecule. The compound may be any diene, diyne or ene-yne compound. Diene, diyne ene-yne compounds are those compounds (including polymeric compounds) wherein there are at least two aliphatic unsaturated groups with some separation between the groups within the molecule. Typically, the unsaturation groups are at the termini of the compound, or pendant if part of a polymeric compound. Compounds containing terminal or pendant unsaturated groups can be represented by the formula $R^2$—Y—$R^2$ where $R^2$ is a monovalent unsaturated aliphatic hydrocarbon group containing 2 to 12 carbon atoms, and Y is a divalent organic or siloxane group or a combination of these. Typically $R^2$ is $CH_2=CH-$, $CH_2=CHCH_2-$, $CH_2=C(CH_3)CH_2-$ or $CH\equiv C-$, and similar substituted unsaturated groups such as $H_2C=C(CH_3)-$, and $HC\equiv C(CH_3)-$.

The compound having the formula $R^2$—Y—$R^2$ as component B) may be considered as being a "organic", "hydrocarbon", "organic polymer", "polyether" or "siloxane", or combinations thereof, depending on the selection of Y. Y may be a divalent hydrocarbon, a siloxane, a polyoxyalkylene, a polyalkylene, polyisoalkylene, a hydrocarbon-silicone copolymer, or mixtures thereof.

In one embodiment, the component (B) is selected from an organic compound, herein denoted as ($B^1$), having the formula $R^2$—$Y^1$—$R^2$ where $R^2$ is a monovalent unsaturated aliphatic group containing 2 to 12 carbon atoms and $Y^1$ is a divalent hydrocarbon. The divalent hydrocarbon $Y^1$ may contain 1 to 30 carbons, either as aliphatic or aromatic structures, and may be branched or un-branched. Alternatively, the linking group $Y^1$ in $B^1$ may be an alkylene group containing 1 to 12 carbons. Component ($B^1$) may be selected from α, ω-unsaturated alkenes or alkynes containing 1 to 30 carbons, and mixtures thereof. Component ($B^1$) may be exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 5-hexadiyne (dipropargyl), and 1-hexene-5-yne.

In another embodiment, the component (B) is selected from a $R^2$—$Y^2$—$R^2$ compound where $Y^2$ is a siloxane, herein denoted as ($B^2$). The $Y^2$ siloxane group may be selected from any organopolysiloxane bonded to at east two organic groups having aliphatic unsaturation, designated as $R^2$, to form $R^2$—$Y^2$—$R^2$ structures. Thus, component ($B^2$) can be any organopolysiloxane, and mixtures thereof, comprising at least two siloxane units represented by the average formula $R^2R_mSiO_{(4-m)/2}$
wherein
R is an organic group,
$R^2$ is a monovalent unsaturated aliphatic group as defined above, and
m is zero to 3

The $R^2$ group may be present on any mono, di, or tri siloxy unit in an organopolysiloxane molecule, for example; $(R^2R_2SiO_{0.5})$, $(R^2RSiO)$, or $(R^2SiO_{1.5})$; as well as in combination with other siloxy units not containing an $R^2$ substituent, such as $(R_3SiO_{0.5})$, $(R_2SiO)$, $(RSiO_{1.5})$, or $(SiO_2)$ siloxy units where R is independently any organic group, alternatively a hydrocarbon containing 1 to 30 carbons, alternatively an alkyl group containing 1 to 30 carbons, or alternatively methyl; providing there are at least two $R^2$ substituents in the organopolysiloxane.

Representative, non-limiting, examples of such siloxane based $R^2$—Y—$R^2$ structures suitable as component ($B^2$) include;

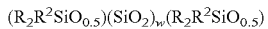

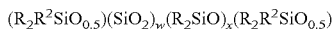

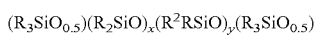

where $w \geq 0$, $x \geq 0$, $y \geq 2$, and $z$ is $\geq 0$, R is an organic group, and
$R^2$ is a monovalent unsaturated aliphatic hydrocarbon group.

$B^2$ may be selected from vinyl functional polydimethylsiloxanes vinyl siloxanes, such as those having the average formula;

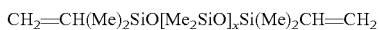

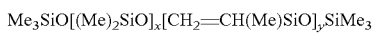

wherein Me is methyl,
$x \geq 0$, alternatively x is 0 to 200, alternatively x is 10 to 100, $y \geq 2$, alternatively y is 2 to 200, alternatively y is 10 to 100. Vinyl functional polydimethylsiloxanes are known, and there are many commercially available.

In another embodiment, component (B) is selected from a polyether compound, herein denoted as ($B^3$), having the formula $R^2$—$Y^3$—$R^2$ compound where $R^2$ is as defined above and $Y^3$ is a polyoxyalkylene group having the formula $(C_nH_{2n}O)_b$ wherein n is from 2 to 4 inclusive,
b is greater than 2,
alternatively b can range from 2 to 100,
or alternatively b can range from 2 to 50.

The polyoxyalkylene group typically can comprise oxyethylene units ($C_2H_4O$), oxypropylene units ($C_3H_6O$), oxytetramethylene or its isomer oxybutylene units ($C_4H_8O$), or mixtures thereof. Thus, the $R^2$—$Y^3$—$R^2$ compound may be selected from a polyoxyalkylene group having the formula $R^2$—O[$(C_2H_4O)_c(C_3H_6O)_d(C_4H_8O)_e$]—$R^2$ where c, d, and e may each independently range from 0 to 100, providing the sum of c+d+e is greater than 2, alternatively the sum of c+d+e ranges from 2 to 100, or alternatively the sum of c+d+e ranges from 2 to 50.

Alternatively, the polyoxyalkylene group comprises only oxypropylene units $(C_3H_6O)_d$. Representative, non-limiting examples of polyoxypropylene containing $R^2$—$Y^3$—$R^2$ compounds include;

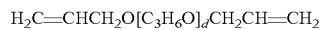

where d is as defined above.

Representative, non-limiting examples of polyoxybutylene containing $R^2$—$Y^3$—$R^2$ compounds include;

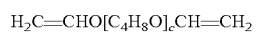

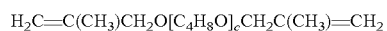

Component B) may also be a mixture of various polyethers, i.e. a mixture of $B^3$ components.

In another embodiment, component (B) is selected from a $R^2$—$Y^4$—$R^2$ compound, herein denoted as ($B^4$), where $R^2$ is as defined above and $Y^4$ is a polyalkylene group, selected from C2 to C6 alkylene units or their isomers. One example is polyisobutylene group which is a polymer containing isobutylene unit. The molecular weight of the polyisobutylene group may vary, but typically ranges from 100 to 10,000 g/mole. Representative, non-limiting examples of $R^2$—Y—$R^2$ compounds containing a polyisobutylene group includes those commercially available from BASF under the tradename of OPPONOL BV, such as OPPONOL BV 5K, a diallyl terminated polyisobutylene having an average molecular weight of 5000 g/mole.

In yet another embodiment, component (B) is selected from a $R^2$—$Y^5$—$R^2$ compound, herein denoted as ($B^5$), where $R^2$ is as defined above and $Y^5$ is a hydrocarbon-silicone copolymer group. The hydrocarbon-silicone copolymer group may have the formula

where $R^1$ and R are as defined above;
u and v are independently $\geq 1$, alternatively u ranges from 1 to 20, alternatively v ranges from 2 to 500, or from 2 to 200,
q is >1, alternatively q ranges from 2 to 500, alternatively q ranges from 2 to 100.

$R^2$—$Y^5$—$R^2$ compounds having a hydrocarbon-silicone copolymer group may be prepared via a hydrosilylation reaction between an α-ω unsaturated hydrocarbon, such as those described above as $B^1$, and an organohydrogensiloxane. A representative, non-limiting example of such a reaction is shown below.

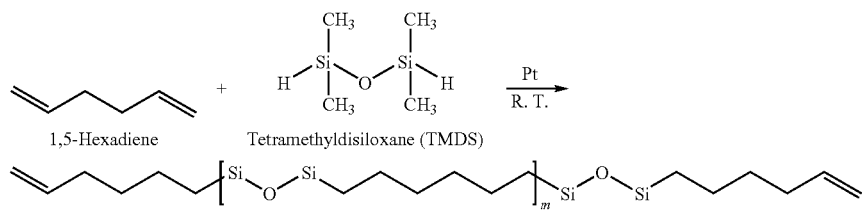

Component (B) may also be a mixture of any diene, diyne or ene-yne compound, such as any combinations of $B^1$, $B^2$, $B^3$, $B^4$, and $B^5$.

The amounts of component (A) and component (B) used to prepare the present composition will depend on the individual components and the desired SiH to aliphatic unsaturation ratio. The ratio of SiH in component (A) to aliphatic unsaturation from component (B) useful to prepare the compositions of the present invention can be from 10:1 to 1:10, alternatively 5:1 to 1:5, or alternatively 4:1 to 1:4.

If components (A) and (B) are not the only materials containing aliphatic unsaturated groups and SiH-containing groups in the present composition, then the above ratios relate to the total amount of such groups present in the composition rather than only those components.

(C) The Hydrosilylation Catalyst

Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601: Lamoreaux, U.S. Pat. No. 3,220,972; Chalk et al., U.S. Pat. No. 3,296,291; Modic, U.S. Pat. No. 3,516,946; Karstedt. U.S. Pat. No. 3,814,730; and Chandra et al U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No, 10/017,229, filed Dec. 7, 2001, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

(D) The Carrier Fluid

The silicone elastomers may be contained in an optional carrier fluid (D). Although it is not required, typically the carrier fluid may be the same as the solvent used for conducting the hydrosilylation reaction as described above. Suitable carrier fluids include silicones, both linear and cyclic, organic oils, organic solvents and mixtures of these. Specific examples of solvents may be found in U.S. Pat. No. 6,200,581 which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 mm$^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy)}trisiloxane pentamethyl{(trimethylsilyl)oxy}cyclotrisiloxane well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H (C11-C12), hydrogenated polydecen. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 0 to 98 weight percent, alternatively 0.5 to 80 weight percent, alternatively 5 to 70 weight percent, of carrier fluid in composition containing (A) and (B) and (D), where the sum of (A), (B), and (D) is 100 weight percent.

E) Personal or Healthcare Active

Component E) is active selected from any personal or health care active. As used herein, a "personal care active" means any compound or mixtures of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Useful active ingredients for use in processes according to the invention include vitamins and its derivatives, including "pro-vitamins". Vitamins useful herein include, but are not limited to, Vitamin $A_1$, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

Component E) may also be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, isopropylbenzyl Salicylate, isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer.

The sunscreen agent can be a single one or combination of more than one. Alternatively, the sunscreen agent is a cinnamate based organic compound, or alternatively, the sunscreen agent is octyl methoxycinnamate, such as Uvinul® MC 80 an ester of paramethoxycinnamic acid and 2-ethylhexanol.

The amount of component E) present in the silicone gel composition may vary, but typically range as follows;

0.05 to 50 wt %, alternatively 1 to 25 wt %, or alternatively 1 to 10 wt %, based on the amount by weight of silicone elastomer gel present in the composition, that is total weight of components A), B), C) and D) in the silicone gel composition.

The active, component E), may be added to the silicone gel or gel paste composition either during the making of the silicone elastomer (pre-load method), or added after the formation of the silicone elastomer gel (post load method). Alternatively, component E) may be post-added to the aqueous emulsion of the gel or gel paste.

The Silicone Elastomer

The silicone elastomers of the present invention are obtainable as hydrosilylation reaction products of components A), B), and C). The term "hydrosilylation" means the addition of an organosilicon compound containing silicon-bonded hydrogen, (such as component A) to a compound containing aliphatic unsaturation (such as component B), in the presence of a catalyst (such as component C). Hydrosilylation reactions are known in the art, and any such known methods or techniques may be used to effect the hydrosilylation reaction of components A), B), and C) to prepare the silicone elastomers of the present invention.

The hydrosilylation reaction may be conducted in the presence of a solvent, and the solvent subsequently removed by known techniques. Alternatively, the hydrosilylation may be conducted in a solvent, where the solvent is the same as the carrier fluid described as optional component D).

Alternatively, the silicone elastomers may be prepared by a process comprising:

I) reacting;
   a) an organohydrogencyclosiloxane having at least two units on a siloxane ring,
   B) a compound or mixture of compounds having at least two aliphatic unsaturated hydrocarbon groups in its molecules,
   C) hydrosilylation catalyst
   with the proviso that at least 10 weight % of B) is an organic compound, to form
   A) an organohydrogensiloxane having at least two SiH containing cyclosilane rings in its molecule,
wherein the molar ratio of the SiH units of component a) to the aliphatic unsaturated groups of component B) ranges from 2/1 to 8/1,
   alternatively from 2/1 to 6/1,
   or alternatively from 3/1 to 4/1,
II) further reacting;
   A) the organohydrogensiloxane having at least two containing cyclosiloxane rings in its molecule, with additional quantities of
   B) the compound containing at least two aliphatic unsaturated groups in its molecules,
   C) the hydrosilylation catalyst.
to form a silicone elastomer.

Components a, A), B), C) are the same as those described above. Also, the reaction may be conducted under similar conditions as described above.

In aforementioned step II) the molar ratio of the SiH units of component A) to the aliphatic unsaturated groups of component B) ranges from 10/1 to 1/10,
   alternatively from 5/1 to 1/5,
   or alternatively from 4/1 to 1/4.

Gelled Compositions Containing the Silicone Elastomer

The silicone elastomers can be added to a carrier fluid (as described above as component D) to form gelled compositions, or alternatively be prepared first in a separate reaction and then added to the carrier fluid to obtain a gel. The gelled compositions of the present invention may be characterized by their hardness or firmness. Useful tests to characterize the gels are those recommended by the Gelatin Manufacturers Institute of America such as the use of a "Texture Analyzer" (model TA.XT2, Stable Micro Systems, Inc., Godalming, England). The gel sample is subject to a compression test with the Texture Analyzer having a probe with a 5.0 kg load cell. The probe approaches the surface of the gel at a speed of 0.5 mm/sec and continues compression into the gel to a distance of 5.0 mm, then holds for 1 second before retreating. The Texture Analyzer detects the resistance force the probe experiences during the compression test. The force exhibited by the load cell is plotted as a function of time.

The hardness of the silicone elastomers, gels and elastomer blends (SEBs) for purposes of this invention is defined as the resistance force detected by the probe of the "Texture Analyzer" during the compression test, Two data may used to characterize hardness: Force 1, the force at the maximum compression point (i.e. the 5.0 mm compression point into the gel surface), and Area F-T: the area-force integration during the 1 second hold at the maximum compression point. The average of a total of 5 tests are typically performed for each gel.

The value obtained for Force 1 is converted into Newton (N), by dividing the gram force value by 101.97. (i.e. 1 Newton equals 101.97 g force based on the size of the probe used in this instrument). The second property reported by Texture Analyzer measurement is Area F-T 1:2, in g force·sec. This is the area integration of the force vs. test time cure. This property is indicative of a gel network since it indicates ability to sustain resistance to the compression force, which is relevant to elastomers and gels. The value is reported in g force·sec, and is converted to Newton·sec in SI unit by dividing the value in g force·sec by 101.97.

The silicone gels of the present invention has a compression hardness of at least 200 Newton/m$^2$, alternatively 400 Newton/m$^2$, or alternatively 600 Newton/m$^2$.

Gel Paste Compositions Containing the Silicone Elastomer

The gelled compositions of the present invention can bused to prepare gel paste or gel blend compositions containing actives by;
   I) shearing the silicone elastomer gel, as described above,
   II) combining the sheared silicone elastomer gel with additional quantities of
   D) the carrier fluid, as described above, and optionally
   E) personal or health care active
to form a gel paste or blend composition.

The silicone elastomer gel compositions of the present invention blends may be considered as discrete crosslinked silicone elastomer gel particles dispersed in carrier fluids. Thus, the silicone elastomer compositions are effective rheological thickeners for lower molecular weight silicone fluids. As such they can be used to prepare useful gel blend compositions, such as "paste" compositions.

To make such silicone elastomer blends, the aforementioned silicone elastomer gels of known initial elastomer content (IEC) are sheared to obtain small particle size and further diluted to a final elastomer content (FEC). "Shearing", as used herein refers to any shear mixing process, such as obtained from homogenizing, sonalating, or any other mixing processes known in the art as shear mixing. The shear mixing of the silicone elastomer gel composition results in a composition having reduced particle size. The subsequent composition having reduced particle size is then further combined with D) the carrier fluid. The earlier fluid may be any carrier fluid as described above, but typically is a volatile methyl siloxane, such as D5. The technique for combining the D) the carrier fluid with the silicone elastomer composition having reduced particle size is not critical, and typically involves simple stirring or mixing. The resulting compositions may be considered as a paste, having a viscosity greater than 100,000 cP (mPa·s).

The emulsions of the present disclosure contain ii) an emulsifier. As used herein, "emulsifier" refers to any compound or substance that enables the formation of an emulsion. The emulsion may be an oil/water emulsion, a water/oil emulsion, a multiple phase or triple emulsion. Thus the emulsifier may be selected from any ionic, nonionic, or zwitterionic surfactant capable of stabilizing emulsions. The surfactant may be an anionic surfactant, cationic surfactant, nonionic surfactant, amphoteric surfactant, or a mixture of surfactants.

Representative examples of suitable anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft N-300. It is a triethanolamine linear alkylate sulphonate composition marketed by the Stephan Company, Northfield, Ill.

Representative examples of suitable cationic surfactants include alkylamine salts, quaternary ammonium salts, sulphonium salts, and phosphonium salts. Representative examples of suitable nonionic surfactants include condensates of ethylene oxide with long chain fatty alcohols or fatty acids such as a $C_{12-16}$ alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, and fatty amine oxides. Representative examples of suitable amphoteric surfactants include imidazoline compounds, alkylamino acid salts, and betaines.

Representative examples of suitable commercially available nonionic surfactants include polyoxyethylene fatty alcohols sold under the tradename BRIJ by Uniqema (ICI Surfactants), Wilmington, Del. Some examples are BRIJ 35 Liquid, an ethoxylated alcohol known as polyoxyethylene (23) lauryl ether, and BRIJ 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40.

When mixtures containing nonionic surfactants are used, one nonionic surfactant should have a low Hydrophile-Lipophile Balance (HLB) and the other nonionic surfactant should have a high HLB, such that the two nonionic surfactants have a combined HLB of 11-15, alternatively a combined HLB of 12.5-14.5.

The emulsifier may also be chosen to form a water/oil or a water/silicone emulsifier, such as silicone polyether emulsifiers. Silicone polyethers (SPEs) generally refer to silicones containing polyether or polyoxyalkylene groups, which could take in many different structural forms. Typically such forms are either rake-type or ABA type SPEs which are derived most commonly from hydrosilylation of SiH functional organosiloxanes with allyloxy-functional polyethers in the presence of a Pt catalyst The silicone polyethers disclosed in U.S. Pat. No. 4,122,029 may be selected as component ii) and is herein incorporated by reference in its entirety for its teaching of polydiorganosiloxanepolyoxyalkylene block copolymers containing at least one polydiorganosiloxane block and at least one polyoxyalkylene block.

An illustrative, non-limiting silicone polyether useful as an emulsifier is

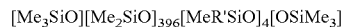

[Me$_3$SiO][Me$_2$SiO]$_{396}$[MeR'SiO]$_4$[OSiMe$_3$]

where Me is —CH$_3$ and R' is —(CH$_2$)$_3$(EO)$_{18}$(PO)$_{18}$OH.

In addition, silicone polyethers useful herein may have the formula

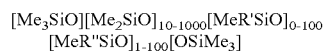

[Me$_3$SiO][Me$_2$SiO]$_{10-1000}$[MeR'SiO]$_{0-100}$
[MeR"SiO]$_{1-100}$[OSiMe$_3$]

where Me is —CH$_3$ and R' is —(CH$_2$)$_3$(EO)$_{18}$(PO)$_{18}$OH, R" is an alkyl group containing 1-40 carbon atoms.

The silicone polyethers disclosed in U.S. Pat. No. 4,853,474 may be selected as component ii and is herein incorporated by reference in its entirety for its teaching of organopolysiloxane-polyoxyalkylene emulsifiers for polar in nonpolar liquid emulsions wherein the organopolysiloxane-polyoxyalkylene polymer molecules are intentionally cross linked through across linking agent joined thereto by non-hydrolyzable bonds and being free of internal hydrolyzable bonds.

Silicone polyether elastomers such as those disclosed in U.S. Pat. No. 5,811,487 may be selected as component ii) and is herein incorporated by reference in its entirety for its teaching of elastomeric silicone polyethers useful as component ii).

The emulsifier may also be a combination or mixture of various emulsifiers, for example any of those described above. The emulsifier may also include the addition of auxiliary surfactants. Furthermore, the emulsifier or mixture of emulsifiers may be used neat, or the emulsifier may be dissolved in a hydrophobic solvent, such as a volatile silicone.

Illustrative, non-limiting commercial products suitable as component ii) include; DC5225C, DC3225C, DC5200, DC9011, DC9040, DC9050 DC8822A, (Dow Corning Corp., Midland, Mich. 48686)

Other additives can also be incorporated in the emulsion, such as fillers, foam control agents anti-freeze agents and biocides.

The emulsions of the present disclosure may be prepared by any known techniques, or alternatively made by the following process;

I) mixing
 i) a gel or gel paste containing a silicone elastomer from the reaction of;
  A) an organohydrogensiloxane having at least two SiH containing cyclosiloxane rings in its molecule,
  B) a compound having at least two aliphatic unsaturated groups in its molecule, and
  C) a hydrosilylation catalyst,
  D) an optional carrier fluid,
  E) an optional personal or healthcare active, and
 ii) an emulsifier,
II) admixing incremental amounts of water to the mixture of step I to form a water continuous emulsion,
III) optionally, shear mixing the water continuous emulsion.

The components in step I of the above process are the same as those described in the preceding sections. Mixing in step (I) can be accomplished by any method known in the art to affect mixing of high viscosity materials. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch equipments with high shear actions include Banbury-type (CW Brabender Instruments Inc., NJ) and Henschel type (Henschel mixers America, TX). Illustrative examples of continuous mixers/compounders include extruders single-screw, twin-screw, and multi-screw extruders, corotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipments.

The temperature and pressure at which the mixing of step I occurs is not critical, but generally is conducted at ambient temperature and pressures. Typically, the temperature of the mixture will increase during the mixing process due to the mechanical energy associated with shearing such high viscosity materials.

Step II of the process involves admixing incremental amounts of water to the mixture of step I to form a water continuous emulsion. Typically 5 to 45 parts water are mixed for every 100 parts of the step I mixture to form a water-continuous emulsion of the elastomeric polymer gel or gel paste having an average particle size less than 5 μm and having sufficient stability to produce a stable lower solids emulsion upon dilution with water.

The amount of water added can vary from 5 to 45 parts per 100 parts by weight of the premix. The water is added to the premix at such a rate so as to form a water continuous emulsion of the elastomeric polymer gel or gel paste. While this amount of water can vary depending on the selection of the gel or gel paste containing a silicone elastomer and emulsifier, generally the amount of water is from 5 to 45 parts per 100 parts by weight of the step I mixture, alternatively from 5 to 30 parts per 100 parts by weight of the step I mixture, or alternatively from 5 to 20 parts per 100 parts by weight of the step I mixture.

Typically the water is added to the premix in incremental portions, whereby each incremental portion comprises less than 8 weight % of the premix and each incremental portion of water is added successively to the previous after the dispersion of the previous incremental portion of water, wherein sufficient incremental portions of water are added to form the water-continuous emulsion of the gel or gel paste containing a silicone elastomer.

Mixing in step (II) can be accomplished by any method known in the art to affect mixing of high viscosity materials. The mixing may occur either as a batch, semi-continuous, or continuous process. Any of the mixing methods as described for step (I), may be used to affect mixing in step (II).

While not to be limited by any theory, the present inventors believe step (II) affects an "inversion" of an oil phase continuous emulsion, formed in step (I), to a water continuous emulsion.

Optionally, the water continuous emulsion formed in step (II) may be further sheared according to step (III) to reduce particle size and/or improve long term storage stability. The shearing may occur by any of the mixing techniques discussed above.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Materials Description
The following materials were used in these examples.
Organohydrogensiloxanes
MeH CYCLICS=methylhydrogen cyclosiloxanes (MeH cyclics) having the formula $[(CH_3)HSiO]_x$ where the average value of x is 4.4.
Siloxane Polymers Containing Unsaturated Groups
VINYL SILOXANE #1=a dimethylhexenylsiloxy-terminated dimethylpolysiloxane of the general formula $(CH_2=CH(CH_2)_4)(CH_3)_2SiO[(CH_3)_2SiO]_{dp}Si(CH_3)_2((CH_2)_4(CH_2=CH))$, where the average degree of polymerization (dp) was 100 and a viscosity of 170 mm$^2$/s at 25° C.
VINYL SILOXANE #2=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 130 and having a viscosity of 325 mm$^2$/s at 25° C.
VINYL SILOXANE #3=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 8 and having a viscosity of 4 mm$^2$/s at 25° C.

α,ω-Unsaturated Polypropylene Oxide
PO20—Polycerin DUS-80=α,ω-diallyl polypropylene oxide having 20 propylene oxide (PO) units from NOF Corporation (Japan).
MPO20—Polycerin DMUS-80=α,ω-dimethallyl polypropylene oxide having 20 propylene oxide (PO) units from NOF Corporation (Japan)
PO50—Unisafe PKA-5018=α,ω-diallyl polypropylene oxide having 50 propylene oxide (PO) units from NOF Corporation (Japan).
Bisallyl PBO=α,ω-diallyl poly(butylene oxide) having the general formula Allyl-(BO)n-PO-(BO)n-Allyl units with a total of about 20 BO units and a molecular weight of about 1600 g/mole, from NOF Corporation (Japan).
Bisallyl PTMG=α,ω-diallyl poly(tetramethylene glycol) having the general formula Allyl-(TMO)n-Allyl units with a total of about 19 TMO units and a molecular weight of about 1500 g/mole, from NOF Corporation (Japan).
Hydrosilylation Catalyst
PT CATALYST=SLY-OFF 4000 (Dow Corning Corporation, Midland Mich.) Pt catalyst used as provided containing 0.52 weight % Pt.
Carrier Fluids
D5 FLUID OR 245 FLUID=decamethylcyclopentasiloxane or D5 cyclics, DC 245 Fluid (Dow Corning Corporation, Midland Mich.) used as provided.
IDNP=isodecyl neopentanoate obtained from ISP (International Specialty Products Co) under the trade name of CERAPHYL SLK.
IDD=isododecane, obtained from Presperse Incorporation (Sumerset, N.J.) under the tradename of Permethyl 99A.
Stabilizer=Vitamin A palmitate (VAP) and butylated hydroxytoluene (BHT)

Example 1 (Reference)

Preparation of an Organohydrogensiloxane Having at Least Two SiH Containing Cyclosiloxane Rings These organohydrogensiloxane were made by charging MeH CYCLICS, VINYL SILOXANE #1 (also denoted as $M^{hex}D_{100}M^{hex}$), and the corresponding carrier fluid into a reaction flask, mixed to homogeneous. Then catalyzed with about 3-5 ppm of Pt using Sly-Off 4000 Pt catalyst solution (containing about 0.52% Pt). The mixture was heated to about 50° C. to cause the exothermic hydrosilylation reaction to occur, and maintained the reaction at a temperature between 50 and 70° C. for about 3 hours. About 0.5% of VAP/BHT (vitamin A palmitate and butylated hydroxytoluene) stabilizer was incorporated once the reaction mixture cooled to below 40° C. The formulations for these compositions and resulting characterizations are summarized in Table 1.

TABLE 1

| Example # | 1A | 1B |
|---|---|---|
| SiH:Vi ratio | 3.42 | 3.42 |
| Alkenyl extender used | $M^{hex}D_{100}M^{hex}$ (VINYL SILOXANE #1) | $M^{hex}D_{100}M^{hex}$ (VINYL SILOXANE #1) |
| Carrier fluid type | D5 fluid | Isododecane |
| Wt. % H, theoretical | 0.0289 | 0.0289 |
| Actual amount | | |
| MeH CYCLICS, g | 14.78 | 29.56 |
| $M^{hex}D_{100}M^{hex}$ (VINYL SILOXANE #1), g | 285.22 | 570.44 |

TABLE 1-continued

| Example # | 1A | 1B |
|---|---|---|
| D5 fluid, g | 300.0 | |
| Isododecane (IDD), g | | 597.0 |
| Sly-Off 4000 catalyst | 0.35 | 0.26 |
| VAP/BHT stabilizer, g | 1.50 | 3.00 |
| Total Batch, g | 601.85 | 1200.26 |
| Mixture appearance | Clear, slightly yellowish mixture | Clear, slightly yellow mixture |

Example 2 (Reference)

Preparation of a Hydrocarbon/Silicone Copolymer as a Component B) and a Component A) Based on it A silicone hydrocarbon with diallyl functionality at ends ($\alpha,\omega$-dihexenyl hydrocarbon oligomers) was prepared by reacting 1,5-hexandiene and tetramethylsiloxane (TMDS) according to the composition in Table 2, Example #2A and Example 2B are made in D5 Fluid, as illustrated in the table. Example #2A1 and Example #2B1 are made also to similar compositions except that they are made in IDD fluid.

TABLE 2

| | Example # | |
|---|---|---|
| | 2A | 2B |
| SiH/vinyl ratio | 0.875 | 3.42 |
| Wt % Organics in diene | 41.1 | 32.7 |
| Wt % Vinyl in dienes | 1.691 | |
| Wt. % H, theoretical | | 0.120 |
| Wt. % H, actual | | 0.124 |
| Composition | | |
| 1,5-Hexadiene, g | 61.67 | |
| Tetramethyldisiloxane, g | 88.33 | |
| MEH CYCLICS, g | | 25.63 |
| Example 2A $\alpha,\omega$-diene (50% conc.), g | | 199.74 |
| D5 Fluid, g | 150.00 | 25.63 |
| Sly-Off 4000, g | 0.125 | 0.144 |
| VAP stabilizer, g | | 0.25 |
| Total Batch, g | 300.12 | 251.39 |
| Mixture appearance | Clear fluid | slightly yellow clear fluid |

Example 3 (Reference)

Preparation of Silicone Elastomer Gels

Representative silicone elastomer gels were prepared using hydrosilyation reactions with the formulations summarized in the following Table 3. The total of components (A) and (B) constitutes the gel network, and is called initial elastomer content (IEC) in the gels in this disclosure. The type and the amount of cosmetic fluid, which is the component D are shown below.

TABLE 3

Silicone elastomer gels from SiH-functional cyclosiloxanes

| | Example # | |
|---|---|---|
| | 3A | 3B |
| Gel composition description | 10% EC Si gel in D5 | 17% EC Si gel in D5 |
| Component A) SiH Int. | Example 1A | Example 1A |
| Vinyl extender type | VINYL SILOXANE #2 | VINYL SILOXANE #2 |
| Carrier fluid type | D5 Fluid | D5 Fluid |
| Composition | | |
| Example 1A (50% conc.), g | 14.67 | 21.48 |
| VINYL SILOXANE #2, g | 22.743 | 40.26 |
| D5 Fluid, g | 262.7 | 238.29 |
| Syl-Off 4000 catalyst, g | 0.25 | 0.17 |
| Total Batch, g | 300.36 | 300.21 |
| Property | | |
| Gel appearance | Clear firm gel | Clear firm gel |
| Texture analyzer, force 1, g | 28.4 | |
| Texture analyzer, force-time 1-2, g | 163.1 | |
| Gel hardness (as compression strength), N/m2 | 2,198 | |
| Viscosity of gel, N · s/m2 or poise (dyne · s/cm2) | 12,624 | |

Elastomer gels are prepared according to these steps: 1) charge all the components except catalyst to a glass container (or a reactor) and stir to homogeneous; 2) Charge the catalyst to the mixture, place the catalyzed mixture in a 70° C. water bath with stirring until the mixture gelled; and 3) keep the reaction mixture in the 70° C. for a total of 4 hrs.

A Texture Analyzer was used to characterize the property of elastomer gels. A detailed description of the test method can be found in previous ID submission or obtained from the inventor. Gel hardness, which is determined is a measure of gel compression stress strength, is calculated using the formula: the value of force 1 from TA is firstly divided by 101.97 to convert from gram force to Newton unit, then divided by $1.267\times10^{-4}$ m$^2$ area of the TA probe, the result is in Newton/m$^2$. Another term "Viscosity of Gel" also introduced, which is derived by dividing the value of Force-time 1-2 by 101.97, then by $1.267\times10^{-4}$ m$^2$; the result in Newton·second/m$^2$ or poise (dyne·s/cm$^2$). The gel hardness and the viscosity of these silicone polyether gels are found in the table attached.

Example 4 (Reference)

Preparation of Silicone Polyether Elastomer Gels

In the case of silicone polyether elastomers, a diallyl or dimethallyl functional polyether is used to form a elastomer gel network with selected % organic content. The organic polyether content may vary depending on the choice of SiH organohydrocyclosiloxane and the polyether component. Shown in the following table are three silicone polyether gels made in D5 fluid.

TABLE 4

| | Example # | | |
|---|---|---|---|
| | 4A | 4B | 4C |
| SiH Int. | Example 1A | Example 1A | Example 1A |
| Vinyl extender type | Polycerin DUS-80 PO20 | Polycerin DMUS-80 MPO20 | Bisallyl PBO |
| Wt. % Organics in gel | 30.9 | 30.3 | 20.1 |
| Carrier fluid type | D5 Fluid | D5 Fluid | D5 Fluid |
| SiH:Vi ratio | 0.80 | 0.80 | 0.80 |
| Composition | | | |
| SiH int Example 1A (50% conc.), g | 70.47 | 71.02 | 81.42 |
| Polycerin DUS-80, g | 15.78 | | |
| Polycerin DMUS-80, g | | 15.50 | |
| Bisallyl-PBO, g | | | 10.29 |
| 245 Fluid, g | 213.79 | 213.62 | 208.34 |
| Syl-Off 4000, g | 0.17 | 0.17 | 0.17 |
| Total Batch, g | 300.20 | 300.31 | 300.22 |
| Property | | | |
| Gel appearance | Clear firm gel | Clear firm gel | Clear firm gel |

Example 5 (Reference)

Preparation of Silicone Organic Elastomer

A representative silicone organic elastomer gel was prepared from a hexenyl terminated SiH siloxane to form a elastomer gel network with selected % organic content. The details of silicone organic elastomer gel preparation can be found in PCT/US07/006936.

TABLE 5

Silicone elastomer gel from Si-organic compound

| | Example # | |
|---|---|---|
| | 5A | 5B |
| Batch description | 20% IEC silicone gel in D5 Fluid | 25% IEC silicone gel in IDD |
| SiH Int. | Example 2B | Example 2B1 |
| Vinyl extender type | Example 2A | Example 2A1 |
| Wt. % Organics in gel | 39.1 | 38.0 |
| Carrier fluid type | 245 Fluid | IDD |
| SiH:Vi ratio | 0.92 | 0.90 |
| Actual amount | | |
| Example 2B (for 5A) or Example 2B1 (for 5B)(50% conc.), g | 31.66 | 12.78 |
| Example 2A (for 5A) or Example 2A1 (for 5B) (50% conc.), g | 68.35 | 27.22 |
| D5 Fluid or IDD, g | 150.00 | 40.07 |
| Syl-Off 4000, g | 0.15 | 0.05 |
| Total Batch, g | 250.16 | 80.12 |
| Gel appearance | Soft clear gel | Clear, hard gel |

Example 6 (Reference)

Preparation of Silicone Elastomer Pastes

Silicone elastomer pastes were made according to the following steps: 1) subject silicone gels from previous examples to mechanical shearing or grinding to reduce gels into finite particle size; 2) dilute with additional cosmetic fluid to desired final elastomer content (FEC), 3) incorporate an optional an vinyl-functional quencher, VINYL SILOXANE #3, and subject the mixture to 70° C. for 2 hrs to effectively scavenging any residual SiH in the mixture. The wt % FEC is the total of components (A) and (B) in elastomer blend, where the total of components (A), (B), and (C) being 100 parts.

Two silicone elastomer blends in D5 Fluid were made according to the above method. Both elastomer blends have 10 or lower elastomer gel content in D5 Fluid: one from an elastomer gel having 10% elastomer content, the other from an elastomer gel having 17% elastomer content. The composition and property of these elastomer blends are found in the following table.

TABLE 6

Silicone elastomer blend compositions

| | Example # | |
|---|---|---|
| | 6A | 6B |
| SEB description | Si elastomer blend made to 10% FEC in D5 Fluid | Si elastomer blend made to 8.2% FEC in D5 Fluid |
| SEB composition: | | |
| Gel example ID | Example 3A | Example 3A |
| % IEC in gel | 10% | 17% |
| Elastomer gel, g | 50.03 | 140.0 |
| D5 Fluid, g | 0 | 150.0 |
| Total (g) | 50.03 | 290.0 |
| % FEC in final elastomer blend | 10.0 | 8.21% |
| Appearance: | Clear paste | Clear paste |
| Viscosity, cps | 976,150 | |
| Particle size: | | |
| D (v, 0.5), um | 8.11 | |
| D (v, 0.9), um | 57.03 | |
| Span | 6.88 | |

Example 7 (Reference)

Preparation of Silicone Polyether Elastomer Pastes

Silicone polyether elastomer blend in cosmetic fluids can be prepared from silicone polyether gels, according to this invention. To make silicone polyether elastomer blend, a silicone polyether gel of known initial elastomer content (IEC) is first prepared following the procedure shown above. The silicone polyether gel is then mechanically sheared or ground into small particle sizes, followed by further dilution with a cosmetic fluid to desired final elastomer content (FEC). The finished elastomer blend is an anhydrous dispersion of SPE gel particles of finite size swollen and suspended in cosmetic fluid. The SPE elastomer blend is clear and has a paste-like consistency.

Silicone polyether elastomer blends are made according to the following steps: 1) subject silicone polyether gels from previous examples to mechanical shearing or grinding to reduce Eels into finite particle size; 2) dilute with additional cosmetic fluid to desired final elastomer content (FEC); 3) incorporate an optional an vinyl-functional quencher, VINYL SILOXANE #3, and subject the mixture to 70° C., for 2 hrs to effectively scavenging any residual SiH in the mixture. The wt % FEC is the total of crosslinked, non-volatile components in elastomer blend.

TABLE 7

Silicone polyether elastomer blend compositions

| | Example # | | |
|---|---|---|---|
| | 7A | 7B | 7C |
| SEB description | Si-Polyether elastomer blend from diallyl PO, made to 10.5% FEC in D5 Fluid | Si-Polyether elastomer blend from dimethallyl MPO, made to 9.28% FEC in D5 Fluid | Si-Polyether elastomer blend from diallyl PBO, made to 10.5% FEC in D5 Fluid |
| % Organics in gel SEB composition: | 31% | 30% | 20% |
| Elastomer gel ID | Example 4A | Example 4B | Example 4C |
| % IEC: | 17% | 17% | 17% |
| Elastomer gel, g | 185.00 | 164.00 | 185.00 |
| D5 Fluid, g | 114.00 | 136.00 | 114.00 |
| Total, g | 299.00 | 300.00 | 299.00 |
| % FEC | 10.52% | 9.29% | 10.52% |
| Appearance: | Clear paste | Slightly hazy paste | Clear paste |

Example 8 (Reference)

Preparation of Silicone Organic Elastomer Blend

Silicone organic elastomer blend in cosmetic fluids can be prepared from silicone organic gels, according to this invention. To make silicone organic elastomer blend, a silicone organic gel of known initial elastomer content an is first prepared following the procedure shown above. The silicone polyether gel is then mechanically sheared or ground into small particle sizes, followed by further dilution with a cosmetic fluid to desired final elastomer content (FEC). The finished elastomer blend is an anhydrous dispersion of Si-Organic gel particles of finite size swollen and suspended in cosmetic fluid. The Si-Organic elastomer blend is clear and has a paste-like consistency.

TABLE 8

Silicone organic elastomer blend compositions

| | Example # | |
|---|---|---|
| | 8A | 8B |
| SEB description | Si-Organic elastomer blend from hexenyl-terminated dienes, made to 13.9% FEC in 245 Fluid | Si-Organic elastomer blend from hexenyl-terminated dienes, made to 11% FEC in IDD |
| % Organics in gel SEB composition: | 39% | 38% |
| Elastomer gel ID | Example 5A | Example 5B |
| % IEC | 20% | 25% |
| Elastomer gel, g | 210.0 | 44.0 |
| 245 Fluid, g | 90.0 | |
| IDD, g | | 56.0 |
| Total, g | 300.0 | 100.0 |
| % FEC | 14.0% | 11.0% |
| Appearance: | Clear paste | Clear paste |

Example 9

Preparation of Nonionic Emulsions of Silicone Elastomer Blends

Water-continuous emulsions of silicone elastomer blend were prepared according to the following steps:
1. Incorporate the surfactants of choice into the SEB, mix under high shear to homogeneous. When more than one surfactant is used. The surfactant of lower HLB value (Brij 30 in this case) is incorporated first and mix to homogeneous using a high shear device such as Hauschild Mixer. The surfactant of higher HLB value (Reflex 30 in this case) is incorporated. A high-shear mixer like Hauschild Mixer is preferred, as the starting SEB is typically has a paste-like consistency.
2. De-ionized water is incorporated into the above SEB/surfactants mixture. Water in small amount installments are added, followed by high shear mixture till the mixture inverts into a water-continuous mixture. The amount of water required to effect inversion is typically called inversion water. Additional water is added to the inverted mixture till a desired wt, % solids is obtained.
3. The as-prepared emulsions are subject to additional high-shear process to reduce the size of emulsions or to improve the consistency of the emulsion. A Microfluidizer from Microfluidics is used to process these emulsions. The property before and after Microfluidizer processing are shown below.

TABLE 9

Emulsion of silicone elastomer blend using non-ionic surfactants

| | Example # 9 |
|---|---|
| Component A: SEB description | Silicone elastomer blend, made to 8.2% FEC in 245 Fluid |
| Emulsion composition: | |
| Component A: SEB type | Example 3B |
| Component A: SEB amount, g | 48.47 |
| Component B: Brij 30, g | 0.45 |
| Component B: Renex 30, g | 1.32 |
| Component C: D.I. water, g | 49.88 |
| Batch total, g | 100.12 |
| Emulsion property: As emulsified in Hauschild Mixer | |
| D(v, 0.5), um | 11.67 |
| D(v, 0.9), um | 49.83 |
| span | 4.25 |
| After additional high-shear process via Microfluidizer | |
| Emulsion appearance | Homogeneous milky |
| % SEB content (component A) | 50.0 |
| D(v, 0.5), μm | 1.71 |
| D(v, 0.9), μm | 4.70 |

Example 10

Preparation of Nonionic Emulsions of Silicone Elastomer Blends

Water-continuous emulsions of silicone polyether and silicone organic elastomer blends were prepared, according to the procedure described above. Illustrated in the following table are the example of these emulsions and their properties.

TABLE 10

Emulsion of silicone elastomer blend using non-ionic surfactants

| | Example # | | |
|---|---|---|---|
| | 10A | 10B | 10C |
| Component A: SEB description | Silicone polyether elastomer blend derived from dimethallyl MPO, made to 9.28% FEC in D5 Fluid | Silicone polyether elastomer blend derived from diallyl PBO, made to 10.5% FEC in D5 Fluid | Silicone organic elastomer blend derived from hexenyl-terminated diene, made to 13.9% FEC in D5 Fluid |
| Emulsion composition | | | |
| Component A: SEB type | Example 7B | Example 7C | Example 8A |
| Component A: SEB amount, g | 48.87 | 48.57 | 48.66 |
| Component B: Brij 30, g | 0.44 | 0.45 | 0.44 |
| Component B: Renex 30, g | 1.33 | 1.32 | 1.32 |
| Component C: D.I. water, g | 49.87 | 49.88 | 49.84 |
| Batch total, g | 100.51 | 100.22 | 100.26 |
| Emulsion property: As emulsified in Hauschild Mixer | | | |
| D(v, 0.5), um | 5.48 | 1.60 | 3.00 |
| D(v, 0.9), um | 30.69 | 8.05 | 10.08 |
| span | 5.58 | 4.66 | 3.18 |
| After additional high-shear process via Microfluidizer | | | |
| Emulsion appearance | Homogeneous milky | Homogeneous milky | Homogeneous milky |
| % SEB content (component A) | 50.0 | 50.0 | 50.0 |
| pH of the emulsion | 6.11 | 5.38 | 4.4 |
| D(v, 0.5), μm | 1.67 | 0.71 | 1.19 |
| D(v, 0.9), μm | 4.19 | 2.31 | 2.07 |
| span | 2.36 | 3.04 | 1.21 |

Example 11

Preparation of Cationic Emulsions of Silicone Elastomer Blends

1. Water-continuous cationic emulsions of silicone elastomer blend, silicone polyether elastomer blend, and silicone organic elastomer blend were prepared according to the following steps: Incorporate the surfactants of choice into the SEB, mix under high shear to homogeneous. When more than one surfactant is used. The surfactant of lower HLB value or non-ionic surfactant (Brij 30 in this case) is incorporated first and mix to homogeneous using a high shear device such as Hauschild Mixer. The surfactant of higher HLB value or ionic surfactant (Arquad 16-29 in this case, incorporated. A high-shear mixer like Hauschild Mixer is typical, as the starting SEB is typically has a paste-like consistency.
2. De-ionized water is incorporated into the above SEB/ surfactants mixture. Water in small amount installments are added, followed by high shear mixture till the mixture inverts into a water-continuous mixture. The amount of water required to effect inversion is typically called inversion water. Additional water is added to the inverted mixture till a desired wt. % solids is obtained.
3. The as-prepared emulsions are subject to additional high-shear process to reduce the size of emulsions or to improve the consistency of the emulsion. A Microfluidizer from Microfluidics is used to process these emulsions. The property before and after Microfluidizer processing are shown below.

TABLE 11

Emulsion of silicone elastomer blend using cationic surfactants

| | Example # | | |
|---|---|---|---|
| | 11A | 11B | 11C |
| Component A: SEB type and composition | Example 6A: silicone elastomre blend made to 8% FEC in 245 Fluid | Example 7A: silicone polyether elastomer blend made to 9.2% FEC in 245 Fluid | Example 8B: silicone organic elastomer blend made to 11% FEC in IDD |
| SEB example ID | Example 6A | Example 7A | Example 8B |
| SEB amount, g | 38.03 | 38.00 | 38.08 |
| Brij 30, g | 4.08 | 3.08 | 3.06 |
| Arquad 16-29, g | 12.03 | 9.07 | 9 |
| D.I. water, g | 46.35 | 50.14 | 49.98 |
| Total, g | 100.49 | 100.29 | 100.12 |
| Emulsion Property: As emulsified in Hauschild Mixer | | | |
| D(v, 0.5), um | 1.26 | 18.96 | 0.27 |
| D(v, 0.9), um | 6.80 | 53.42 | 6.42 |
| Span | 5.27 | 2.80 | 23.57 |
| After additional high shear process through Microflidizer | | | |
| appearance | Homogeneous | Homogeneous | Homogeneous |
| pH of emulsion | 7.50 | 4.74 | 7.04 |
| D(v, 0.5), μm | 0.22 | 0.42 | 0.21 |
| D(v, 0.9), μm | 0.33 | 1.12 | 1.56 |

Example 12

Preparation of Anionic Emulsions of Silicone Elastomer Blends

Water-continuous anionic emulsions of silicone elastomer blend, silicone polyether elastomer blend, and silicone organic elastomer blend are prepared according to the following steps:
1. Incorporate the surfactant of choice into the SEB, mix under high shear to homogeneous. A high-shear mixer like Hauschild Mixer is preferred, as the starting SEB is typically has a paste-like consistency.
2. De-ionized water is incorporated into the above SEB/surfactants mixture. Water in small amount installments are added, followed by high shear mixture till the mixture inverts into a water-continuous mixture. The amount of water required to effect inversion is typically called inversion water. Additional water is added to the inverted mixture till a desired wt. % solids is obtained.
3. The as-prepared emulsions are subject to additional high-shear process to reduce the size of emulsions or to improve the consistency of the emulsion. A Microfluidizer from Microfluidics is used to process these emulsions. The property before and after Microfluidizer processing are shown below.

TABLE 12

Emulsion of silicone elastomer blend using anionic surfactants

| | Example # | | |
|---|---|---|---|
| | 12A | 12B | 12C |
| Component A: SEB type and composition | Example 6A: silicone elastomer blend made to 8% FEC in 245 Fluid | Example 7A: silicone polyether elastomer blend made to 9.2% FEC in 245 Fluid | Example 8B: silicone organic elastomer blend made to 11% FEC in IDD |
| | Emulsion Composition: | | |
| SEB example ID | Example 6A | Example 7A | Example 8B |
| SEB amount, g | 44.1 | 44.3 | 44.0 |
| SLES surfactant, g | 6.0 | 6.1 | 6.0 |
| D.I. water, g | 50.1 | 49.8 | 50.1 |
| Total, g | 100.2 | 100.1 | 100.1 |
| | Emulsion Property: As emulsified in Hauschild Mixer | | |
| D(v, 0.5), um | 7.95 | 5.90 | 1.42 |
| D(v, 0.9), um | 17.49 | 20.18 | 16.8 |
| Span | 2.06 | 3.36 | 11.68 |
| | After additoinal high shear process through Microflidizer | | |
| Appearance of emulsion | Homogeneous | Cream layer atop overtime, but easily remixed to homogeneous | Cream layer atop overtime, but easily remixed to homogeneous |
| D(v, 0.5), μm | 0.78 | 0.74 | 0.69 |
| D(v, 0.9), μm | 1.44 | 1.30 | 1.97 |
| Span | 1.53 | 1.43 | 2.66 |

Example 13

Preparation of OMC Sunscreen Loaded Silicone Polyether Elastomer Blends

Personal care and healthcare actives, particularly hydrophobic actives, may be incorporated into the silicone or silicone organic elastomer blends. The active containing elastomer blends are further emulsified into a water-continuous emulsion, according to the current invention.

Illustrated in the following table are examples of 2-ethylhexyl methoxycinnamate (OMC) sunscreen containing elastomer blends that were derived by incorporating OMC into elastomer blends derived from gels of the hydrosilylation reaction of SiH intermediate polymer and diallyl poly(oxybutylene), poly(oxytetramethylene) polyethers in either 245 Fluid or IDD. The elastomer blends contain about 20 wt. % OMC and about 10 wt. % EC.

Four elastomer polyether elastomer gels, of about 30-32% organic content, are prepared using two hydrophobic polyethers to react with 100 dp siloxane of Example 1 in two different carrier fluids.

| | Experiment gel ID | | | |
|---|---|---|---|---|
| | 13A | 13B | 13C | 13D |
| SiH Int. | Example 1A | Example 1A | Example 1B | Example 1B |
| Vinyl extender type | Bisallyl PBO | Bisallyl PTMG | Bisallyl PBO | Bisallyl PTMG |
| Wt. % Organics in gel | 31.6 | 30.1 | 32.0 | 30.5 |
| Carrier fluid type | 245 Fluid | 245 Fluid | IDD | IDD |
| SiH:Vi ratio | 0.90 | 0.90 | 0.90 | 0.90 |

-continued

| | Experiment gel ID | | | |
|---|---|---|---|---|
| | 13A | 13B | 13C | 13D |
| Actual amount | | | | |
| Example 1A (50% solids in D5, g | 69.80 | 70.78 | | |

-continued

| | Experiment gel ID | | | |
|---|---|---|---|---|
| | 13A | 13B | 13C | 13D |
| Example 1A (50% solids in IDD), g | | | 69.40 | 70.86 |
| Bisallyl PBO, g | 16.11 | | 16.30 | |
| Bisallyl PTMG, g | | 15.61 | | 15.58 |
| 245 Fluid, g | 214.104 | 213.718 | | |
| Isododecane, g | | | 214.333 | 213.635 |
| Syl-Off 4000, g | 0.17 | 0.17 | 0.17 | 0.17 |
| Total Batch, g | 300.19 | 300.28 | 300.21 | 300.24 |
| Gel appearance | Clear firm gel | opaque white soft gel | Clear firm gel | slightly hazy firm gel |

| | Experiment gel ID | | | |
|---|---|---|---|---|
| | 13A | 13B | 13C | 13D |
| Texture analyzer, force 1, g | 271.2 | 245.4 | 102.0 | 195.1 |
| Texture analyzer, force-time 1-2, g | 1437.6 | 1301.7 | 552.9 | 1048.6 |
| Gel hardness (as compression strength), N/m2 | 20,994 | 18,993 | 7,897 | 15,102 |

OMC is incorporated into these silicone polyether gels to give silicone organic elastomer blends with about 20% OMC content and a 9.5-10% FEC. The composition of these elastomer blends are shown below.

TABLE 13

OMC sunscreen loaded silicone elastomer blends

| | Example # | | | |
|---|---|---|---|---|
| | 13E | 13F | 13G | 13H |
| Component A: SEB description | OMC loaded SOEB derived from bisally PBO, made to 9.9% FEC in 245 Fluid | OMC loaded SOEB derived from bisallyl PTMG, made to 10.0% FEC in 245 Fluid | OMC loaded SOEB derived from bisallyl PBO, made to 9.9% FEC in IDD fluid | OMC loaded SOEB derived from bisallyl PTMG, made to 9.5% FEC in IDD fluid |
| | | SEB composition | | |
| Elastomer gel ID | 13A | 13B | 13C | 13D |
| Elastomer gel, g | 56.00 | 56.09 | 56.04 | 56.04 |
| IDD, g | | | 19.99 | 25.13 |
| 245 Fluid, g | 20.07 | 20.04 | | |
| OMC active, g | 20.05 | 19.01 | 20.03 | 19.03 |
| Total, g | 96.12 | 95.14 | 96.06 | 100.20 |
| | Elastomer blend property | | | |
| % FEC in blend | 9.9% | 10.0% | 9.9% | 9.5% |
| % OMC active | 20.0% | 20.0% | 20.9% | 19.0% |
| Appearance | Hazy opaque paste | Opaque white | Clear colorless paste | Clear colorless paste |
| D (v, 0.5), μm | 232.1 | 98.8 | 195.2 | 100.9 |
| D (v, 0.9), μm | 524.1 | 208.6 | 389.2 | 224.9 |
| Span | 1.95 | 1.64 | 1.61 | 1.77 |
| Viscosity, cps | 931,149 | 450,774 | 407,047 | 294,417 |

Example 14

Preparation of Emulsion of OMC Sunscreen Loaded Silicone Polyether Elastomer Blends The following SOEBs are made for this series of examples:

| | Michelle's ID: | | |
|---|---|---|---|
| | 14A | 14B | 14C |
| Component A: SEB description | OMC loaded SOEB derived from bisallyl PBO, made to 9.9% FEC in IDD fluid | OMC loaded SOEB derived from bisallyl PTMG, made to 10.0% FEC in 245 Fluid | OMC loaded SOEB derived from bisallyl PBO, made to 9.9% FEC in 245 Fluid |
| | | SEB composition: | |
| Elastomer gel type | 13C | 13B | 13A |
| Elastomer gel, g | 56.04 | 56.09 | 56.00 |
| IDD, g | 19.99 | | |

-continued

| | Michelle's ID: | | |
|---|---|---|---|
| | 14A | 14B | 14C |
| 245 Fluid, g | | 20.04 | 20.07 |
| OMC active, g | 20.03 | 19.01 | 20.05 |
| Total, g | 96.06 | 95.14 | 96.12 |
| Elastomer blend property | | | |
| % FEC in blend | 9.9% | 10.0% | 9.9% |
| % OMC active | 20.9% | 20.0% | 20.0% |
| Appearance | Clear colorless paste | Opaque white | Hazy opaque paste |
| D (v, 0.5), μm | 195.2 | 98.8 | 232.1 |
| D (v, 0.9), μm | 389.2 | 208.6 | 524.1 |
| Span | 1.61 | 1.64 | 1.95 |
| Avg viscosity, cps | 407,047 | 450,774 | 931,149 |

Emulsions of OMC sunscreen containing silicone poly her elastomer blends were prepared according to the following steps:

1. Incorporate the surfactant(s) into the SEB, mix under high shear to homogeneous. A high-shear mixer like Hauschild Mixer is preferred, as the starting SEB is typically has a paste-like consistency. When two surfactants are used, the surfactant with lower HLB value is usually incorporated first into SEB, mix to homogeneous; then the higher HLB surfactant is dispersed under shear to the mixture.
2. De-ionized water is incorporated into the above SEB/surfactants mixture, Water in small amount installments are added, followed by high shear mixture till the mixture inverts into a water-continuous mixture. The amount of water required to effect inversion is typically called inversion water. Additional water is added to the inverted mixture till a desired wt. % solids is obtained.
3. The as-prepared emulsions are subject to additional high-shear process to reduce the size of emulsions or to improve the consistency of the emulsion. A Microfluidizer from Microfluidics is used to process these emulsions. The property before and after Microfluidizer processing are shown below.

TABLE 14

| Emulsions of OMC sunscreen loaded silicone elastomer blends | | | |
|---|---|---|---|
| | Example # | | |
| | 14D | 14E | 14F |
| Component A: SEB description | OMC loaded silicone polyether elastomer blend derived from Bisally PBO, made to 9.9% FEC in IDD fluid | OMC loaded silicone polyether elastomer blend derived from Bisallyl PTMG, made to 10.0% FEC in 245 Fluid | OMC loaded silicone polyether elastomer blend derived from Bisallyl PBO, made to 9.9% FEC in 245 Fluid |
| Emulsion composition: actual | | | |
| Component A: SEB batch | 14A | 14B | 14C |
| SEB amount, g | 49.98 | 50.02 | 50.08 |
| Component B: Brij 30, g | 0.90 | 0.93 | 0.95 |
| Component B: Renex 30, g | 2.70 | 2.70 | 2.76 |
| D.I. water, g | 49.10 | 46.39 | 46.60 |
| Batch total, g | 102.67 | 100.04 | 100.39 |
| Emulsion Property: As emulsified in Hauschild Mixer | | | |
| D(v, 0.5), um | 0.28 | 0.28 | 0.27 |
| D(v, 0.9), um | 2.08 | 0.61 | 2.69 |
| Span | 6.94 | 1.58 | 9.36 |
| After additoinal high shear process through Microflidizer | | | |
| Emulsion appearance | Homogeneous | Homogeneous | Homogeneous |
| D(v, 0.5), μm | 0.58 | 0.29 | 0.67 |
| D(v, 0.9), μm | 2.01 | 2.84 | 3.53 |

The invention claimed is:

1. An aqueous emulsion composition comprising:
   i) a gel having a compression hardness of at least 200 Newton/m² containing a silicone organic elastomer from the reaction of;
   A) an organohydrogensiloxane prepared by a hydrosilylation reaction of;
      a) an organohydrogencyclosiloxane having the formula $[(CH_3)HSiO]_g$ where g is 3-8 and,
   B) a compound or mixture of compounds having at least two aliphatic unsaturated hydrocarbon groups in its molecule selected from a vinyl functional or hexenyl functional polydimethylsiloxane having the average formula;

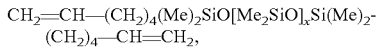

or

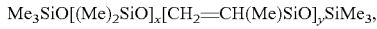

wherein Me is methyl, x≧0 and y≧2, and
   wherein the molar ratio of SiH units to unsaturated group ranges from 2/1 to 8/1,
   B³) a polyether compound or mixture of polyether compounds having the formula $R^2$—Y—$R^2$ where $R^2$ is a monovalent unsaturated aliphatic group and Y is a polyoxyalkylene group having the formula $—[(C_2H_4O)_c(C_3H_6O)_d(C_4H_8O)_e]—$ where c, d, and e and may each independently range from 0 to 200, providing the sum of c+d+e is greater than 2 and
   C) a hydrosilylation catalyst,
   D) fluid, and
   ii) an emulsifier.

2. The emulsion of claim 1 further comprising;
   E) personal or healthcare active.

3. The emulsion of claim 1 wherein the emulsion is an oil/water emulsion having an internal oil phase comprising i) the gel and a continuous aqueous phase.

4. The emulsion of claim 3 wherein the emulsion contains;
   5 to 90 weight percent of the internal oil phase,
   0.5 to 20 weight percent of the emulsifier,
   and sufficient water to sum to 100 weight percent.

5. A process for preparing an aqueous emulsion comprising:
   I) mixing
      i) a gel having a compression hardness of at least 200 Newton/m² containing a silicone organic elastomer from the reaction of;
      A) an organohydrogensiloxane prepared by a hydrosilylation reaction of;
         a) an organohydrogencyclosiloxane having the formula $[(CH_3)HSiO]_g$ where g is 3-8 and,
      B) a compound or mixture of compounds having at least two aliphatic unsaturated hydrocarbon groups in its molecule selected from a vinyl functional or hexenyl functional polydimethylsiloxane having the average formula;

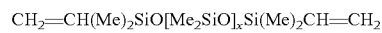

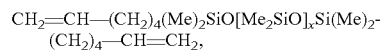

or

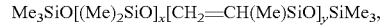

wherein Me is methyl, x≧0 and y≧2, and
      wherein the molar ratio of SiH units to unsaturated group ranges from 2/1 to 8/1,
      B³) a polyether compound or mixture of polyether compounds having the formula $R^2$—Y—$R^2$ where $R^2$ is a monovalent unsaturated aliphatic group and Y is a polyoxyalkylene group having the formula $—[(C_2H_4O)_c(C_3H_6O)_d(C_4H_8O)_e]—$ where c, d, and e may each independently range from 0 to 200, providing the sum of c+d+e is greater than 2
      C) a hydrosilylation catalyst, and
      D) carrier fluid,
      E) an optional personal or healthcare active, and
      ii) an emulsifier,
   II) admixing incremental amounts of water to the mixture of step I to form a water continuous emulsion,
   III) optionally, shear mixing the water continuous emulsion.

6. The aqueous emulsion prepared according to the method of claim 5.

* * * * *